United States Patent
Neuvonen et al.

(10) Patent No.: US 10,434,310 B2
(45) Date of Patent: Oct. 8, 2019

(54) IMPLANTABLE STIMULATION DEVICE

(71) Applicant: Sooma Ltd., Helsinki (FI)

(72) Inventors: Tuomas Neuvonen, Espoo (FI); Jani Virtanen, Söderkulla (FI); Mika Nikader, Helsinki (FI)

(73) Assignee: Sooma Ltd., Helsinki (FI)

( * ) Notice: Subject to any disclaimer, the term of this patent is extended or adjusted under 35 U.S.C. 154(b) by 127 days.

(21) Appl. No.: 15/322,433

(22) PCT Filed: Jun. 30, 2015

(86) PCT No.: PCT/EP2015/064907
§ 371 (c)(1),
(2) Date: Dec. 27, 2016

(87) PCT Pub. No.: WO2016/001261
PCT Pub. Date: Jan. 7, 2016

(65) Prior Publication Data
US 2017/0136239 A1    May 18, 2017

Related U.S. Application Data

(60) Provisional application No. 62/019,173, filed on Jun. 30, 2014.

(51) Int. Cl.
*A61N 1/36* (2006.01)
*A61N 1/05* (2006.01)

(52) U.S. Cl.
CPC ....... *A61N 1/36025* (2013.01); *A61N 1/0531* (2013.01); *A61N 1/0534* (2013.01); *A61N 1/0539* (2013.01); *A61N 1/36017* (2013.01)

(58) Field of Classification Search
USPC .......................................... 607/45
See application file for complete search history.

(56) References Cited

U.S. PATENT DOCUMENTS

| | | | |
|---|---|---|---|
| 6,529,774 B1 | 3/2003 | Green | |
| 2005/0075680 A1* | 4/2005 | Lowry | A61N 1/0531 607/45 |
| 2007/0179558 A1 | 8/2007 | Gliner et al. | |
| 2008/0312716 A1 | 12/2008 | Russell | |

OTHER PUBLICATIONS

WIPO, U.S. International Preliminary Examining Authority, International Preliminary Report on Patentability dated Oct. 13, 2016 in International Patent Application No. PCT/EP2015/064907, 9 pages.
Wipo, U.S. International Search Authority, International Search Report and Written Opinion dated Sep. 8, 2015 in International Patent Application No. PCT/EP2015/064907, 12 pages.

* cited by examiner

*Primary Examiner* — Nicole F Lavert
*Assistant Examiner* — Nicole F Johnson
(74) *Attorney, Agent, or Firm* — Inskeep IP Group, Inc.

(57) ABSTRACT

A conductive implantable stimulation device for implantation at the head of a subject to treat a neurological disease, comprising a first passive conductive member, wherein the first member is sized and configured for being implanted under the skull bone of the patient, and wherein the first member comprises a conductive interface adapted for extracranial stimulation.

11 Claims, 5 Drawing Sheets

IMPLANTABLE STIMULATION DEVICE

RELATED APPLICATIONS

This application is the U.S. National Phase of and claims priority to International Patent Application No. PCT/EP2015/064907, International Filing Date Jun. 30, 2015, entitled An Implantable Stimulation Device, which claims benefit of U.S. Provisional Application Ser. No. 62/019,173 filed Jun. 30, 2014 entitled Conductive Implantable Stimulation Device, both of which are incorporated herein by reference in their entireties.

BACKGROUND OF THE INVENTION

Field of the Invention

This invention pertains in general to the field of stimulation devices, and especially to conductive implantable stimulation devices.

Description of the Prior Art

Transcranial direct current stimulation (tDCS) is a non-invasive technique that can be used to modulate brain activity and to promote neuroplastic changes for therapeutic aims. Recent advances include therapeutic success in major depression treatment, potential in chronic pain treatment and stroke rehabilitation. Specific targeting of electrical current is hampered by the skull, which has poor conductivity. This is a well-known problem in brain bio-electromagnetism. The skull thickness and conductivity properties are unknown, which makes the prediction of current flow into the brain a very difficult task that require detailed measurements and modelling of electrical properties of the anatomy and structure of brain and skull.

Moreover, in animal studies with tDCS has been shown that nearly 50% of the electrical current of tDCS does not reach the brain, but rather flows from anode to cathode on the skull 11 surface. Therefore, the output current from the device needs to be increased to reach a desired target levels in the target brain tissue. This, in turn, creates complications such as adverse sensations, skin irritation and possibly skin burns.

In chronic diseases, such as Parkinson's disease or chronic pain, one potential treatment approach is to implant a deep brain stimulation (DBS) device (Parkinson's) or an epidural motor cortex stimulator (MCS, chronic pain). In DBS, the electrodes are installed close to deep brain structures (subthalamic nucleus or globus pallidus) to specifically target these structures. In MCS, the aim is to reach specific cortical areas to modulate cortical activity associated with the pain relief. Installation of a DBS electrode is expensive and can lead to serious adverse effects, such as stroke, cerebral infections. Moreover, technically complicated equipment requires periodical maintenance, battery charging or changing that needs to be completed in an operation. Similar complications are present in the MCS implantation.

Thus, a need for an improved stimulation device solving or at least mitigating the above problems is needed.

SUMMARY OF THE INVENTION

Accordingly, embodiments of the present invention preferably seeks to mitigate, alleviate or eliminate one or more deficiencies, disadvantages or issues in the art, such as the above-identified, singly or in any combination by providing a device according to the appended patent claims.

According to a first aspect of the invention a conductive implantable stimulation device for implantation at the head of a subject to treat a neurological disease, comprising a first passive conductive member, wherein the first member is sized and configured for being implanted under the skull bone of the patient, and wherein the first member comprises a conductive interface adapted for extracranial stimulation.

According to a second aspect of the invention a stimulation system for treatment of neurological diseases in a patient, comprising an electrical extracranial stimulator and at least one first passive conductive member, wherein the first member is sized and configured for being implanted under the skull bone of the patient, and wherein the first member comprises a conductive interface adapted for receiving extracranial stimulation from the extracranial stimulator.

According to a third aspect of the invention a method of stimulating a desired brain region, comprising applying an extracranial stimulation to an conductive implantable stimulation device, wherein the device comprises a first passive conductive member, wherein the first member is sized and configured for being implanted under the skull bone of the patient, and wherein the first member comprises a conductive interface adapted for the extracranial stimulation.

Further embodiments of the invention are defined in the dependent claims, wherein features for the second and subsequent aspects of the invention are as for the first aspect mutatis mutandis.

Some embodiments of the invention provide for creating electric current in a conductive material.

Some embodiments of the invention provide for a device for implantation into or at the skull of a patient.

Some embodiments of the invention provide for stimulators stimulating a conductive implantable stimulation device.

Some embodiments of the invention provide for treatment of a neurological disease.

Some embodiments of the invention provide for a member sized and configured for being implanted under the skull bone of the patient.

Some embodiments of the invention provide for a device effectively eliminating or at least significantly reducing an electrical resistance (impedance) of the skull.

Some embodiments of the invention provide for stimulation of more current at a pre-set voltage stimulation value to a desired treatment area in the brain.

Some embodiments of the invention provide for larger current than when a current is applied directly to the head of a patient.

Some embodiments of the invention provide for a more effective and powerful stimulation.

Some embodiments of the invention provide for an increased accuracy of current delivery (location and amplitude).

Some embodiments of the invention provide for stimulation without skull effects.

Some embodiments of the invention provide for the possibility to use lower currents for stimulation.

Some embodiments of the invention provide for further decreasing potential side-effects to the patient.

Some embodiments of the invention provide for a member sized and configured for being implanted under the scalp of the patient.

Some embodiments of the invention provide for even larger induced currents than with only a first member.

Some embodiments of the invention provide for an electrical field being larger due to a closer proximity.

Some embodiments of the invention provide for a greater current also at a first member.

Some embodiments of the invention provide for an overall improved effect.

Some embodiments of the invention provide for an anode and a cathode.

Some embodiments of the invention provide for a single integrated member which acts as booth an anode and a cathode.

Some embodiments of the invention provide for a device to be implanted by a minimally-invasively.

Some embodiments of the invention provide for a small incision to the skin and a small hole to the skull.

Some embodiments of the invention provide for no need to service or maintenance.

Some embodiments of the invention provide for reduced postoperative complications.

Some embodiments of the invention provide for no stimulator or battery to be implanted inside the skull.

Some embodiments of the invention provide for covering a large target area in the brain.

Some embodiments of the invention provide for separation and placement at separate desired locations in the skull.

Some embodiments of the invention provide for a biosensor as a feedback or in a feedback control system when stimulating.

Some embodiments of the invention provide for measurements in e.g. accuracy and/or effect.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the disclosure are capable of will be apparent and elucidated from the following description of examples of the present disclosure, reference being made to the accompanying drawings, in which.

DESCRIPTION OF THE PREFERRED EMBODIMENTS

Figure 1:
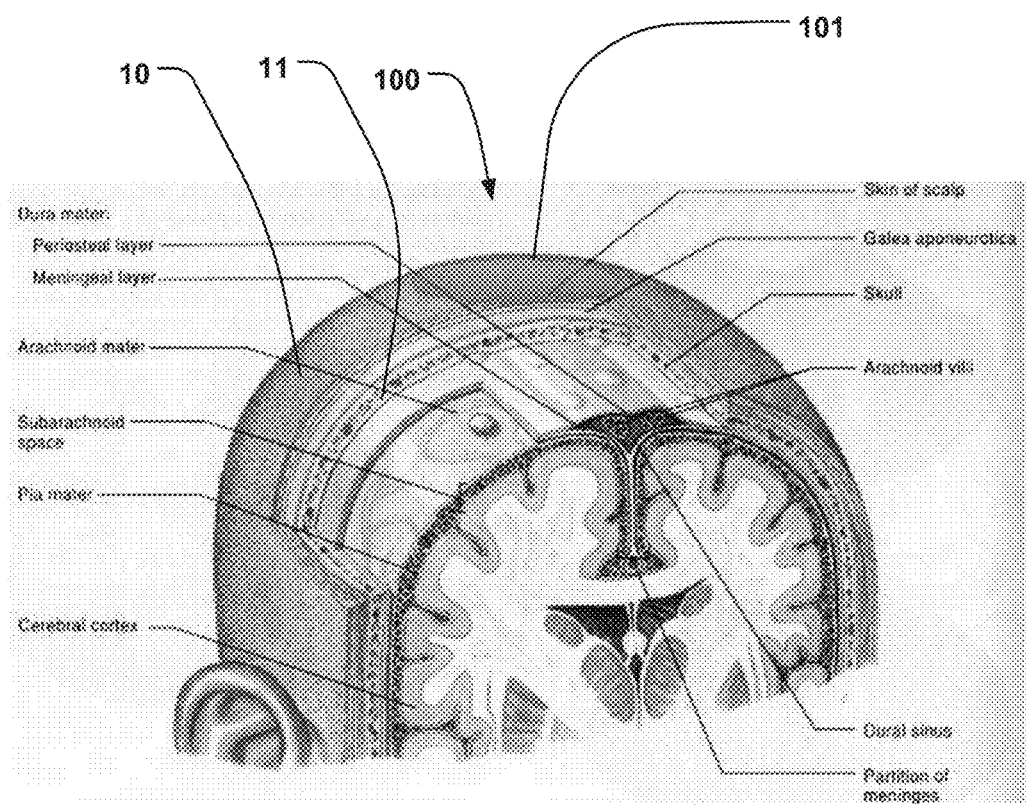
FIG. 1 is a side view of a schematic drawing of a stimulator for neurological diseases.

Specific examples of the disclosure will now be described with reference to the accompanying drawings. This invention may, however, be embodied in many different forms and should not be construed as limited to the examples set forth herein. Rather, these examples are provided so that this disclosure will be thorough and complete, and will fully convey the scope of the invention to those skilled in the art. The terminology used in the detailed description of the examples illustrated in the accompanying drawings is not intended to be limiting of the invention. In the drawings, like numbers refer to like elements.

Figure 2:
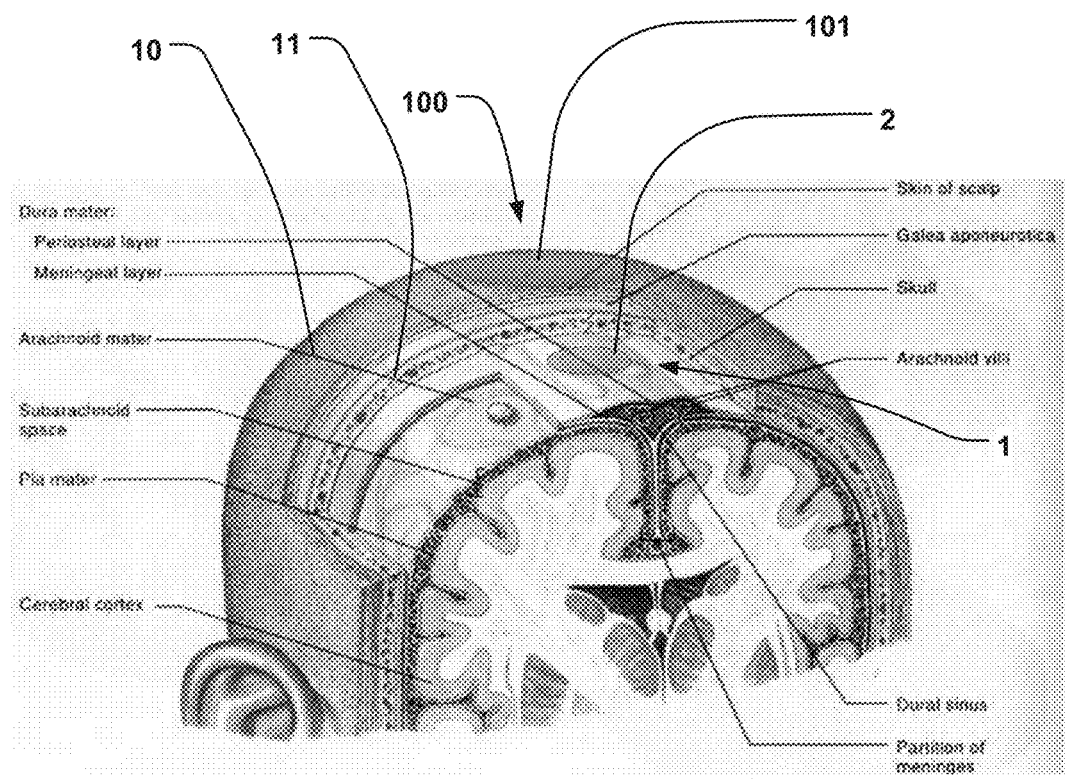
FIG. 2 is a side view of a schematic drawing of a conductive implantable stimulation device comprising a first member implanted under the skull of a patient.
Figure 3:
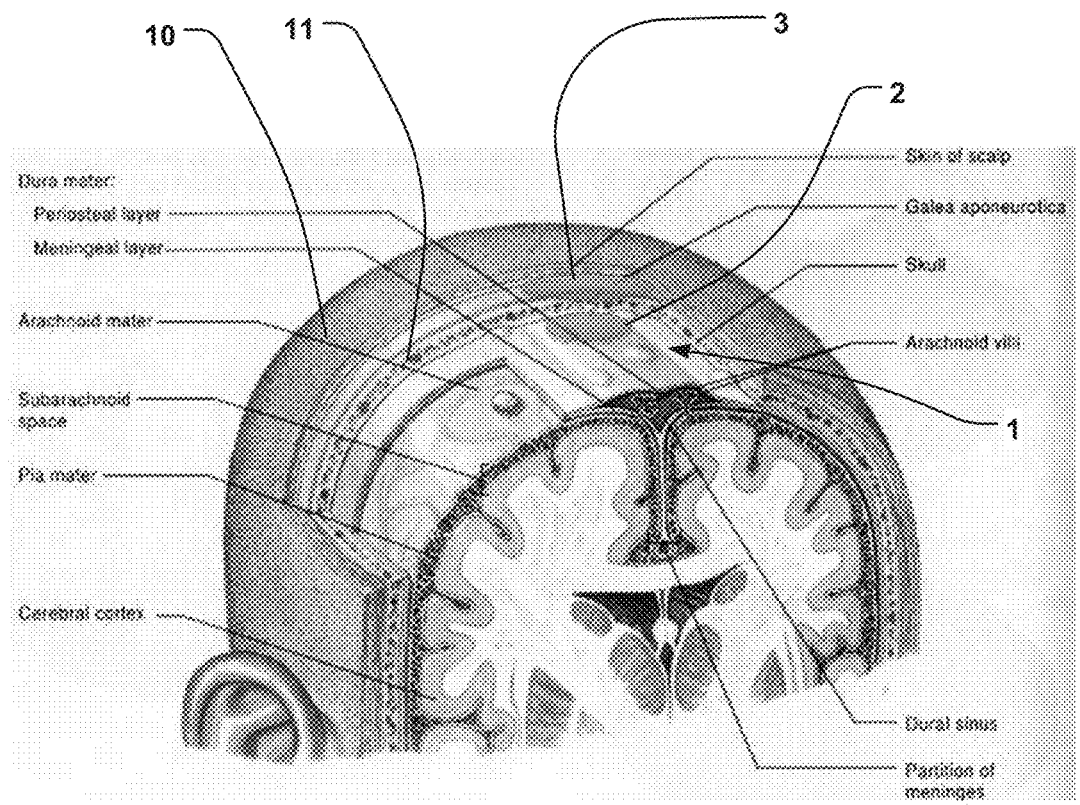
FIG. 3 is a side view of a schematic drawing of a conductive implantable stimulation device 1 comprising a first member implanted under the skull of a patient and a second member implanted under the skin of the patient.

The following description focuses on an example of the present disclosure applicable to a conductive implantable stimulation device FIG. 1 discloses an electrical stimulator 101 for neurological diseases. The stimulator 101 is in an example a direct current stimulator 101 such as a pulsed direct current stimulator 101 or a transcranial direct current stimulator 101 (tDCS), in another example an alternating current (AC) stimulator 101. AC and pulsed DC create magnetic fields that, by inductance, create electric current in a conductive material such as comprised in a device for implantation into or at the skull 11 of a patient. Such stimulators 101 are in an example stimulating a conductive implantable stimulation device 1 for implantation at the head of a subject to treat a neurological disease, as seen in FIGS. 2-5. The implantable stimulation device 1 comprises a first passive conductive member 2, as seen in FIG. 2. The first member is sized and configured for being implanted under the skull 11 bone of the patient, and the first member comprises a conductive interface adapted for extracranial stimulation. By having a conductive implantable stimulation device 1 comprising a first passive conductive implant, the device effectively eliminates or at least significantly reduces an electrical resistance (impedance) of the skull 11 and thus conducts more current at a pre-set voltage stimulation value to a desired treatment area in the brain when exposed to the pre-set voltage stimulation. Thus, the current being induced in the first member, by the extracranial stimulations electrical field, is larger than when a current is applied directly to the head of a patient and wherein the current need to pass through the skin, skull 11 and brain all having a large and complex impedance, to its desired treatment region. Hence, a more effective and powerful stimulation is achieved when having a first member, an increased accuracy of current delivery (location and amplitude) without skull 11 effects and/or the possibility to use lower currents for stimulation further decreasing potential side-effects to the patient. In examples the conductive interface is preferably adapted to receive AC, pulsed DC or non-pulsed DC.

In an example, the first member 2 comprises a coil for wirelessly coupling the first member 2 to the stimulator 101. By having the first member comprising a coil under the skull (or in the skull) the first member is made like an RFID-type of component comprising a coil and its function is generally also based on induction like the RFID component. By then to applying a required DC or AC thru a partially or a completely implanted first member 2 comprising an induction coil current is easily delivered to the brain. Hence, coupling is made wirelessly.

In an example the conductive implantable stimulation device 1 comprises a second passive conductive member 3. The second member is sized and configured for being implanted under the scalp 10 of the patient. The conductive implantable stimulation device 1 may also comprise a third passive conductive member 4 and the third member is connected to the first and second members. The second member comprises a conductive interface adapted for receiving extracranial stimulation and conduct the extracranial stimulation to the first member through the third member. By having a second member arranged under the scalp 10, the induced current in the second member is even larger than with only the first member, since the electrical field is larger at the second member due to a closer proximity and/or electrical field of the stimulation need only to pass through the scalp 10 and not also the skull 11. This gives a greater current also at the first member because the third member connects and passes the current on from the second member to the first member, thus giving an overall improved effect. This configuration makes it also possible to use non-pulsed DC for the stimulation. In an example the third member 4 is expandable such that the third member 4 expands into contact with the first 2 and/or second member 3. By having the third member 4 expand into contact with the other two members 2, 3 it is possible to have a third member which adapts to the surroundings, i.e. the skull when connecting the two members 2 and 3.

In an example the third member 4 comprises is a locking mechanism for the first member 2 such that the third member 4 is locked into and secured to the first member 2. In an example the second member 3 and the third member 4 are integrally formed and the third member 4 comprises the locking mechanism for locking and securing to the first member 3. In an example the second 3 and third member 4 is integrally formed and the third member 4 is expandable as described above.

In an example the third member 4 or second member 3 comprises a docking member for docking the member 3 or 4 to stimulator 101.

Figure 4A:
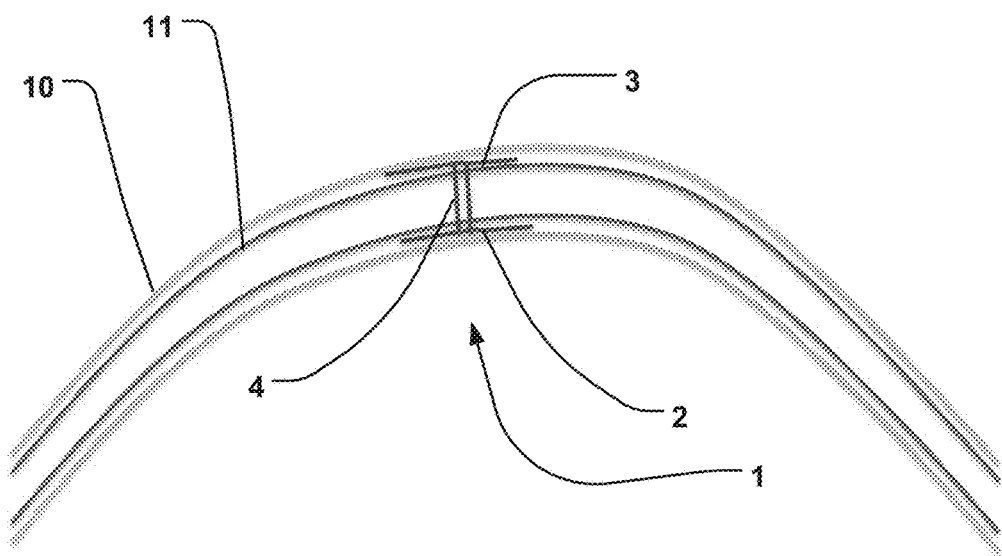
FIGS. 4a and 4b are side views of a conductive implantable stimulation device comprising a first, second and third member.
Figure 4B:
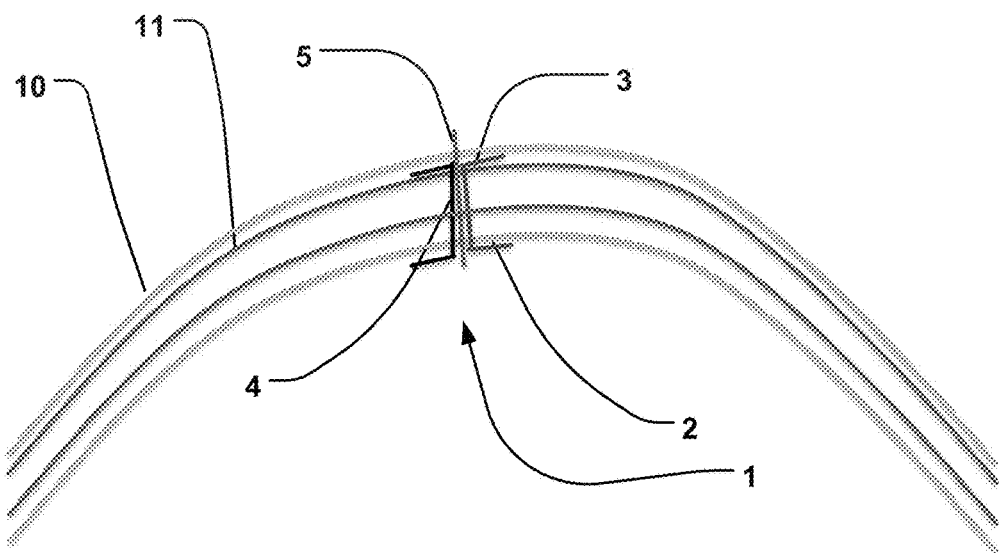
Figure 5A:
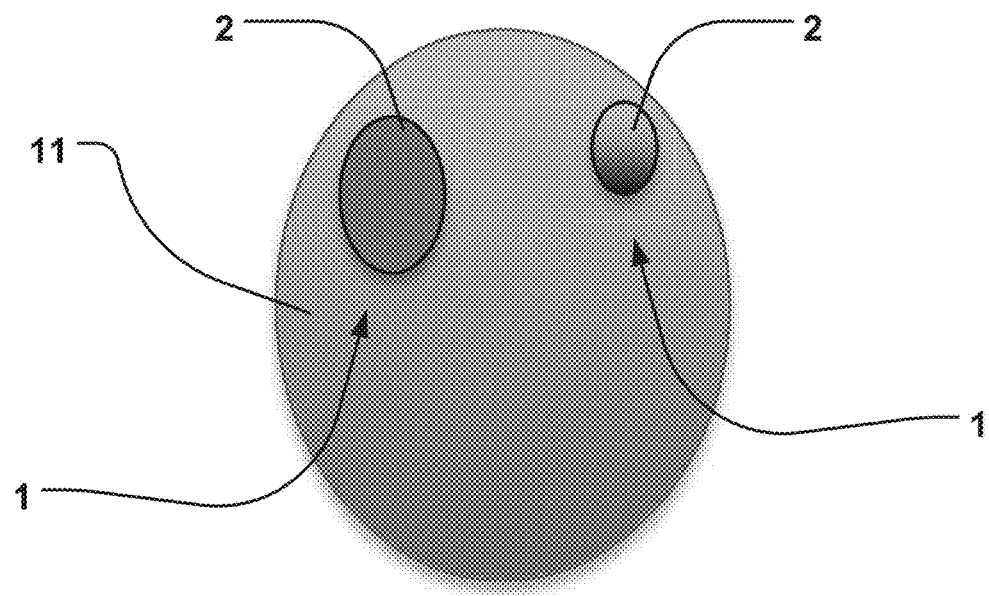
FIGS. 5a and 5b are top views of a conductive interface of a conductive implantable stimulation device.
Figure 5B:
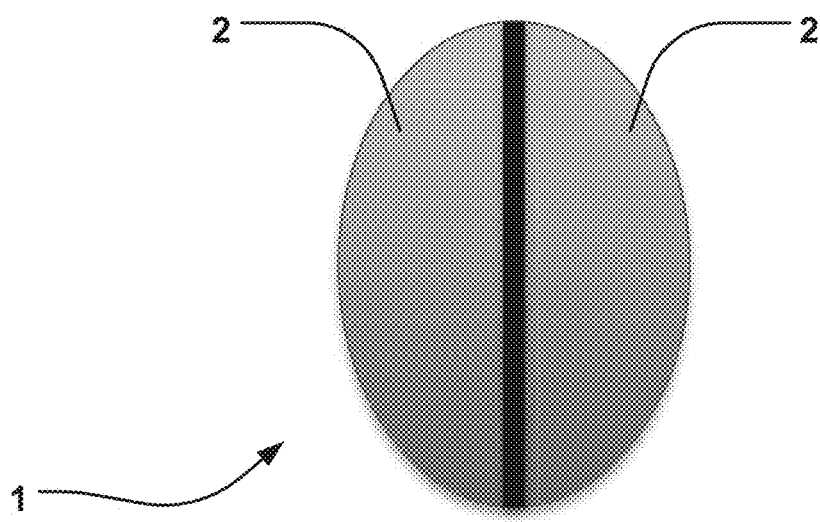

In an example the first, second and third member comprises an isolator 5 for configuring an anode and a cathode, as illustrated in FIG. 5*b*. By having an isolator 5 in the first, second and third members it is possible to have a single integrated member which can act as booth the anode and the cathode when stimulating the brain of the patient. In an example the first, second and third members are integral. In an example the isolator 5 is common to all members, as illustrated in FIG. 4*b*. In an example, the first 2, second 3, and/or third 4 member comprises several anodes and/or cathodes. In an example, the anodes and/or cathodes are configured by a common isolator 5 or by several isolators 5. In examples, the isolators 5 are configured in each of the first 2, second 3 or third members 4, or in a combination of first 2, second 3 and third 4 members such as first and second 2, 3, first and third 2, 4 and second and third 3, 4.

In an example first, second and/or third members are sized and configured to be implanted by a minimally-invasive introducer. By having the implantable stimulation device 1 sized and configured to be implanted minimally-invasively only a small incision to the skin is needed and a small hole to the skull 11 as well, similar to what is done in epidural electrode installations. As a result, the system will have a simple implantable stimulation device 1 with virtually no need for service or maintenance and/or reduced postoperative complications as implantation can be done in the epidural space and no stimulator 101 or battery will be implanted inside the skull 11.

In an example the first 2 and/or second 3 and/or third member 4 comprises a diode for allowing the current (AC or DC) to float only in one direction. In an example the diode is diode or diode-type of a material that allows current to flow only in one direction.

In an example a stimulation system 100 for treatment of neurological diseases in a patient is disclosed comprising an electrical extracranial stimulator 101 and at least one first passive conductive member 2. The first member is sized and configured for being implanted under the skull 11 bone of the patient, and the first member comprises a conductive interface adapted for receiving extracranial stimulation from the extracranial stimulator 101.

In yet an example the stimulation system 100 additionally comprises at least one second passive conductive member 3 and at least one third passive conductive member 4. The second member is sized and configured for being implanted under the scalp 10 of the patient and the third member is electrically connected to the first and second members. The second member comprises a conductive interface adapted for receiving the extracranial stimulation and conduct the extracranial stimulation to the first member through the third member.

In an example, the system 100 comprises a first member comprising a coil for coupling and transmitting current like an RFID component.

In an example a first of the at least one first passive conductive member 2 is an anode and a second of the at least one first passive conductive member 2 is a cathode, as illustrated in FIG. 5*a*. By having two first passive conductive members 2, one being the anode and the other being the cathode, it is possible to cover a large target area in the brain since they two first members are separate elements which can be separated independently and placed at separate desired locations in the skull 11. In an example a first of the at least one first, second and third passive conductive member is an anode and a second of the at least one first, second and third passive conductive member is a cathode. By having two first, second and third passive conductive member, one of the first, second and third passive conductive member being the anode and the other first, second and third passive conductive member being the cathode, it is possible to cover a large target area in the brain since they anode and cathode are separate structures and can be separated independently and placed at separate desired locations in the skull 11.

In an example the anode and cathode have a similar size of the conductive interface of the first or second member, as illustrated in FIG. 5*b*. This method can create highly targeted stimulation areas in the brain In an example the cathode have a larger size than the anode, of the conductive interface of the first or second member, as illustrated in FIG. 5*a*. This method allow large area stimulation and/or simultaneous up- and down-regulation of target brain areas.

In an example the electrical extracranial stimulator 101 generates an AC or pulsed DC or non-pulsed DC.

In an example the stimulation system 101 comprises an integrated biosensor arranged in the first, second and/or third member, or in the electrical stimulator 101. By having a biosensor the system can use the biosensor as a feedback or in a feedback control system for the stimulation. Hence, the stimulation can be measured in e.g. accuracy and/or effect. In an example the integrated biosensor is an EEG sensor, a MEG sensor and/or an EMG sensor.

A) If we make the "shunt" part expandable OR if we claim it as a locking mechanism for under the skull component or a docking mechanism for the external stimulator (then it happens to be conductive at the same time)

B) If we make it to consist of several components (e.g. we might have 2 or several conductive sectors [anodes+cathodes]+a 3rd (or nth) sector that could be an insulator between these two unit sections)

C) Several conductive channels placed in a nonconductive unit

D) An implantable conductor comprising a diode allowing the current (AC or DC) to float only in one direction. "diode or diode-type of a material" that allows current to flow only in one direction E) System that does not need the conductive part between the external stimulator and under-the-skull (or in the skull) part. If it is made like RFID-type of a coil→function is generally based on induction. The idea is then to apply required DC or AC thru partially or completely implanted induction coil to the brain. So, coupling is made wirelessly.

In an example a method of stimulating a desired brain region. The method comprises applying an extracranial stimulation to an conductive implantable stimulation device 1. The device comprises a first passive conductive member 2, wherein the first member is sized and configured for being implanted under the skull 11 bone of the patient and the first member comprises a conductive interface adapted for the extracranial stimulation.

In an example a method of stimulating a desired brain region comprises applying an extracranial stimulation to the conductive implantable stimulation device 1 further comprising a second passive conductive member 3. The second member is sized and configured for being implanted under the scalp 10 of the patient. The device also comprises a third passive conductive member 4, wherein the third member is electrically connected to the first and second members. The second member comprises a conductive interface adapted for receiving the extracranial stimulation, and conduct the extracranial stimulation to the first member through the third member.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items.

The present disclosure has been described above with reference to specific examples and experiments. However, other examples than the above described are equally possible within the scope of the disclosure. Different method steps or a different order thereof than those described above may be provided within the scope of the disclosure. The different features and steps of the disclosure may be combined in other combinations than those described. The scope of the disclosure is only limited by the appended patent claims.

The invention claimed is:

1. A conductive implantable stimulation device for implantation in the head of a subject to treat a neurological disease, comprising:
   a first passive conductive member, wherein the first passive conductive member is sized and configured for being partially implanted in and not under the skull bone, and is configured for stimulating a brain of said subject, wherein said first passive conductive member further comprises a first conductive interface that is a coil adapted for receiving extracranial stimulation from an electrical extracranial stimulator;
   a second passive conductive member that is sized and configured for being implanted above said skull bone and under a scalp of said subject, the second passive conductive member comprising a second conductive interface adapted for wireless coupling to the electrical extracranial stimulator so as to receive extracranial stimulation;
   a third passive conductive member that is electrically connected to said first passive conductive member and the second passive conductive member such that the third passive conductive member conducts current from the second passive conductive member to the third passive conductive member; and,
   an isolator positioned through said first passive conductive member, said second passive conductive member, and said third passive conductive member so as to create an anode and a cathode therethrough each.

2. A conductive implantable stimulation device according to claim 1, wherein said first conductive interface is adapted to receive AC, pulsed DC or non-pulsed DC.

3. A conductive implantable stimulation device according to claim 1, wherein saki first passive conductive member, said second passive conductive member, and saki third passive conductive member are integral with each other.

4. A conductive implantable stimulation device according to claim 1, wherein saki first passive conductive member, said second passive conductive member, and saki third passive conductive member are sized and configured to be implanted by a minimally-invasive introducer.

5. A stimulation system for treatment of neurological diseases in a patient, comprising:
   an electrical extracranial stimulator,
   a first passive conductive member, wherein the first member is sized and configured for being implanted under the skull bone of the patient and having a first conductive interface that is a coil adapted for receiving extracranial stimulation from the extracranial stimulator;
   a second passive conductive member that is sized and configured for being implanted above said skull bone and under a scalp of said subject, the second passive conductive member comprising a second conductive interface adapted for wireless coupling to the electrical extracranial stimulator so as to receive extracranial stimulation;
   a third passive conductive member that is electrically connected to said first passive conductive member and the second passive conductive member such that the third passive conductive member conducts current from the second passive conductive member to the third passive conductive member; and,
   an electrical isolator positioned through said first passive conductive member, said second passive conductive member, and said third passive conductive member so as to create an anode and a cathode therethrough each.

6. A stimulation system according to claim 5, wherein the anode and cathode have a similar size of the conductive interface of the first or second member.

7. A stimulation system according to claim 5, wherein the cathode has a larger size than the anode, of the conductive interface of the first or second member.

8. A stimulation system according to claim 5, wherein the electrical extracranial stimulator generates an AC or pulsed DC or non-pulsed DC.

9. A stimulation system according claim 5, comprising an integrated biosensor arranged in said first passive conductive member, said second passive conductive member, and saki third passive conductive member, or in the electrical stimulator.

10. A stimulation system according to claim 5, wherein the integrated biosensor is an EEG sensor, a MEG sensor and/or an EMG sensor.

11. A method of stimulating a desired brain region, comprising:
- applying an extracranial stimulation to an conductive implantable stimulation device, wherein the device comprises:
- a first passive conductive member, wherein the first member is sized and configured for being implanted under the skull bone of the patient and having a first conductive interface that is a coil adapted for receiving extracranial stimulation from the extracranial stimulator;
- a second passive conductive member that is sized and configured for being implanted above said skull bone and under a scalp of said subject, the second passive conductive member comprising a second conductive interface adapted for wireless coupling to the electrical extracranial stimulator so as to receive extracranial stimulation;
- a third passive conductive member that is electrically connected to said first passive conductive member and the second passive conductive member such that the third passive conductive member conducts current from the second passive conductive member to the third passive conductive member; and,
- an electrical isolator positioned through said first passive conductive member, said second passive conductive member, and said third passive conductive member so as to create an anode and a cathode therethrough each.

* * * * *